United States Patent
Plog et al.

(10) Patent No.: US 6,231,734 B1
(45) Date of Patent: May 15, 2001

(54) PROCESS FOR NO-DETECTION IN FLUID MEDIA

(75) Inventors: Carsten Plog; Werner Maunz, both of Markdorf; Ralf Mueller, Aulendorf; Wolfgang Schaefer, Friedrichshafen; Armin Kayser, Meersburg; Ralf Moos, Friedrichshafen; Udo Flesch; Ulrich Simon, both of Essen, all of (DE)

(73) Assignee: Dornier GmbH, Friedrichshafen (DE)

(*) Notice: Subject to any disclaimer, the term of this patent is extended or adjusted under 35 U.S.C. 154(b) by 0 days.

(21) Appl. No.: 09/056,639

(22) Filed: Apr. 8, 1998

(30) Foreign Application Priority Data

Apr. 8, 1997 (DE) ............................................. 197 14 364

(51) Int. Cl.[7] .................................................. G01N 27/407
(52) U.S. Cl. ........................... 204/424; 204/426; 205/781
(58) Field of Search ................................... 204/421, 424, 204/426; 205/781

(56) References Cited

U.S. PATENT DOCUMENTS

| 5,397,442 | | 3/1995 | Wachsman . | |
|---|---|---|---|---|
| 5,409,591 | * | 4/1995 | Baker et al. | 204/425 |
| 5,458,868 | * | 10/1995 | Barrow | 423/600 |
| 5,466,350 | * | 11/1995 | Baker et al. | 204/153.14 |
| 5,552,025 | * | 9/1996 | Coe | 205/785.5 |
| 5,580,433 | * | 12/1996 | Baker et al. | 204/425 |

FOREIGN PATENT DOCUMENTS

170472 * 6/1998 (JP) .

OTHER PUBLICATIONS

Logothetis et al, "High–Temperature Oxygen Sensors Based on Electrochemical Oxygen Pumping", Fundamentals and Applications of Chemical Sensors, Chapter 8, pp. 136–154, American Chemical Society, no month available, 1986.*

* cited by examiner

Primary Examiner—Robert J. Warden, Sr.
Assistant Examiner—Kaj K. Olsen
(74) Attorney, Agent, or Firm—Evenson, McKeown, Edwards & Lenahan, P.L.L.C.

(57) ABSTRACT

A process and apparatus for selective detection of NO in fluid media, particularly exhaust gases of internal-combustion engines. This process comprises the steps of positioning a nitrosonium-conducting solid electrolyte between two porous electrodes, acting upon one of the two electrodes with the NO-containing fluid medium, and measuring a voltage difference between the two electrodes as an indication of the NO-concentration in the NO-containing fluid medium.

9 Claims, 3 Drawing Sheets

PROCESS FOR NO-DETECTION IN FLUID MEDIA

BACKGROUND AND SUMMARY OF THE INVENTION

This application claims the priority of German patent document 197 14 364.4-52, the disclosure of which is expressly incorporated herein.

The invention relates to a process for detecting nitrogen oxide (NO) in fluid media.

Several methods are known for removing nitrogen from diesel engine exhaust gases. A catalytic removal of nitrogen can be carried out by using ammonia or hydrocarbons as reducing agents. Adsorber catalysts can remove nitrogen by the adsorption of $NO_x$, but must be regenerated at regular short intervals by using reducing agents. Also, nitrogen oxide emission can be reduced by returning exhaust gas into the combustion chamber. This effect can be enhanced by enriching the returned exhaust gas with $NO_x$ by using suitable adsorber materials.

But, material-based nitrogen removal processes are based on knowing load-dependent and rotational-speed-dependent momentary $NO_x$-emissions for metering of the reducing agent and the adsorption/regeneration periods. This can take place either by using an NO-sensor or by using characteristic diagram values filed in a memory of a computer.

Characteristic $NO_x$-diagrams do not apply to individual engines but only to series of engines so that fluctuations in the crude $NO_x$-gas content caused by manufacturing may occur while characteristic diagram points are the same. In addition, momentary catalyst condition (temperature, $NO_x$-load and reducing agent load) may be different while characteristic diagram points are the same. An NO-sensor-controlling regulation would therefore be preferred. When an NO-sensor is used, exhaust gas recirculation rate can be controlled such that minimal $NO_x$-emission occurs at each engine operating point.

The literature describes a number of sensors for measurement of NO-content in gases. However, only a few are suitable for conditions in real exhaust gas that is hot.

In principle, ceramic solid electrolytes offer a high potential for the application because they are highly selective, resistant to high temperatures and are not expensive to build. This can be seen by the considerable success of the λ-sensor, an oxygen ion conductor based on zirconia. For this principle to be effective for NO, a solid $NO^+$ electrolyte is required.

U.S. Pat. No. 5,466,350 describes an amperometric thin-film solid-electrolyte detector for NO which is based on the passage of nitrosonium cations ($NO^+$) through the solid electrolyte. Four electrodes are required in a bipotentiostat arrangement: a first and a second working electrode, a joint reference electrode and a joint counter electrode. In addition, a diffusion barrier is used in front of the working electrode acting as the anode; the diffusion barrier provides that the sensor operates under diffusion-controlled conditions. Only in this manner can it be ensured that the output signal is proportional to the NO-concentration in the gas.

In U.S. Pat. No. 5,466,350, a $NO$-$\beta$-$Al_2O_3$ is used as the solid electrolyte and is manufactured in two steps from $Na$-$\beta$-$Al_2O_3$. First, the $Na$-$\beta$-$Al_2O_3$ is exchanged in an $AgNO_3$-melt with $Ag^+$ to $Ag$-$\beta$-$Al_2O_3$. In a second step, $Ag$-$\beta$-$Al_2O_3$ is exchanged with $NO^+$ while utilizing $NOCl$-ions so that finally $NO$-$\beta$-$Al_2O_3$ is obtained. This second step requires a medium which simultaneously has a good solubility for $NO^+$ as well as for $Ag^+$ and good oxidation resistance at temperatures about 200° C.

The state of the art according to U.S. Pat. No. 5,466,350 has the following disadvantages:

The bipotentiostat arrangement uses four electrodes. In contrast to a two-electrode arrangement, this represents a clearly more complicated arrangement with respect to design, manufacturing and operation.

So that the ionic current in the solid electrolyte in an amperometric measuring principle is proportional to the NO-concentration in the gas phase, a diffusion barrier must be integrated.

Furthermore, as the result of the principle, the suggested amperometric sensor principle with the diffusion limitation is slow because it is diffusion-dependent. Also, sensor signal quality depends on sensor surface quality (coating by soot particles). In the real exhaust gas of a motor vehicle, a constant and continuously accurate relation between NO concentration and sensor reading can therefore not be achieved.

In addition, a basic disadvantage of the amperometric measuring principle is cross-sensitivity to water vapor which exists in exhaust gas in high concentrations. Because a voltage of at least 1.6 volts—the literature value of 1.31 V relates to the calomel electrode—is required for the NO-oxidation, reactions with water vapor also may take place on the first working electrode (anode). For example:

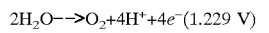

$$2H_2O \rightarrow O_2 + 4H^+ + 4e^- \ (1.229 \text{ V})$$

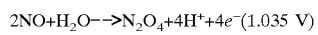

$$2NO + H_2O \rightarrow N_2O_4 + 4H^+ + 4e^- \ (1.035 \text{ V})$$

The Protons formed according to these reactions are also transported through the electrolyte and, like NO, are reduced on the second working electrode, which acts as the cathode. The measured current is therefore composed of the sum of $NO^+$ and $H^+$.

With respect to the manufacture of the $NO^+$-conducting solid electrolyte according to U.S. Pat. No. 5,466,350, there are the following disadvantages:

The suggested manufacturing process for the $NO^+$-conducting solid electrolyte requires working in aggressive, non-hydrolysis-resistant salt melts and is carried out in a very cumbersome manner in several steps. In particular, cleaning of the solid electrolyte after the ion exchange with water and alcohol required when a salt melt is used is problematic and may damage the electrolyte (hydrolysis of NO to $HNO_3$). The limitation to 190° C. (starting decomposition of the NO salt melt) and the concentration difference between the melt and the electrolyte as the only driving force makes the complete ion exchange impossible in dense layers of $\beta''$-$Al_2O_3$. However, gas-tight thin layers of pure $\beta\Delta$-$Al_2O_3$ are necessary for a technical implementation of the results for a fast sensor.

A basic disadvantage of the exchange reactions in the melt or in the solution is that the moving force of the reaction is represented by the formation of insoluble products, such as AgCl when an $Ag^+$-ion conductor is used in an NOCl-containing melt. From preliminary investigations, it is known (R. H. Radzilowski, J. T. Kummer, *Inorg. Chem.*, 8 (1996) 2531; S. Maraun, Diploma thesis, University GH Essen, 1996) that these insoluble residues may precipitate on the solid electrolyte and prevent exchange by passivation. This requires that starting materials are used which are as fine-grained as possible and which, after the exchange, must first be chemically processed and then compacted to molded bodies. As will be illustrated in the following, in the process according to the invention, molded bodies of the desired shape can be used directly.

U.S. Pat. No. 5,466,350 is based on Na-β-$Al_2O_3$. In contrast to Li-stabilized Na-β"-$Al_2O_3$, Na-β-$Al_2O_3$ has a different layer sequence and a resulting lower ion conductivity. In addition, it may be affected by hydrolysis. As a rule, it contains high (>1%) parts of $NaAlO_2$ which is responsible for this water delicacy. A quantitatively complete exchange of $Na^+$ for $Ag^+$ is therefore not possible. The remaining Na results in a strong decomposition due to hydrolysis in real exhaust gas and therefore in a fast destruction of the electrolyte in real exhaust gas.

Summarizing, the following disadvantages exist for implementing a sensor according to U.S. Pat. No. 5,466,359, particularly with a view to motor vehicle applications:

no purely potentiometric measuring principle (λ-sensor); this leads to a slow sensor kinetic and requires an expensive sensor technology and also expensive sensor electronics.

low stability of the solid electrolyte to hydrolysis results in a destruction of the electrolyte during an operation in real exhaust gas;

expensive production process; no complete conversion to an NO-ion conductor is possible.

It is therefore an object of the invention to provide a process for NO-detection in fluid media by means of which the above-mentioned disadvantages of U.S. Pat. No. 5,466, 350 are overcome.

This object is achieved by means of a process for selectively detecting NO in fluid media comprising positioning a nitrosonium ($NO^+$) conducting solid electrolyte between two porous electrodes, acting upon one of the two electrodes with the fluid containing media, and then measuring the voltage difference between the two electrodes. An apparatus is also provided.

The object according to the invention comprises the following process steps:

positioning of a nitrosonium ($NO^+$)-conducting solid electrolyte between two porous electrodes;

acting upon one of the two electrodes with the NO-containing fluid medium, without insertion of a diffusion barrier;

measuring the voltage difference between the two electrodes as an indication of the NO-concentration in the NO-containing fluid medium. An apparatus corresponding to the above process is also provided.

The process according to the invention overcomes the disadvantages of the state of the art in that a potentiometric and not an amperometric measuring is carried out for NO-detection. As a result, only two electrodes are required. In principle, potentiometric sensors achieve a fast signal reaction because no diffusion equilibrium need be adjusted. Also, the measuring signal is independent of changes of the sensor surface which typically occur during operation in real exhaust gas.

Furthermore, instead of being obtained by way of an ion exchange in the salt melt, the $NO^+$-containing solid electrolyte can be obtained directly from a gas phase. This can take place in simple gas-tight reactors and is therefore easy to carry out even in large-scale applications.

The process according to the invention can be used particularly in the exhaust gas of lean-operated as well as λ=1-operated motor vehicles for determining momentary nitrogen oxide concentration.

Other objects, advantages and novel features of the present invention will become apparent from the following detailed description of the invention when considered in conjunction with the accompanying drawings.

DETAILED DESCRIPTION OF THE DRAWINGS

Sensor Construction and Principle of the NO-Detection

Sensor construction is advantageously based on a gas-tight (>98% of the theoretical density) thin disk made of Listabilized Ag-β"-$Al_2O_3$ with a thickness of, for example, 200 μm. By means of a connecting layer (such as glass solder), this disk is mounted on a metallized metallic ceramic pedestal. The connection takes place in a soldering process at a temperature of at most 1,000° C. based upon the melting temperature of the selected glass solder. The connection with the pedestal must be gas-tight and non-conductive. Pastes, CVD- or PVD-layers can be used as the electrodes. The layers should be of a low thickness in order to permit a fast gas diffusion to the electrolyte surface. The electrode material may particularly be graphite, noble metal semi-metal, semiconductor or electronically conductive ceramics. The contacting may take place by way of noble metal contacts.

If the $Ag^+$ for $Na^+$ ion exchange is conducted in an Ag melt, the silver precipitated on the cathode or remaining on the anode takes over the function of the electrode.

Figure 4:
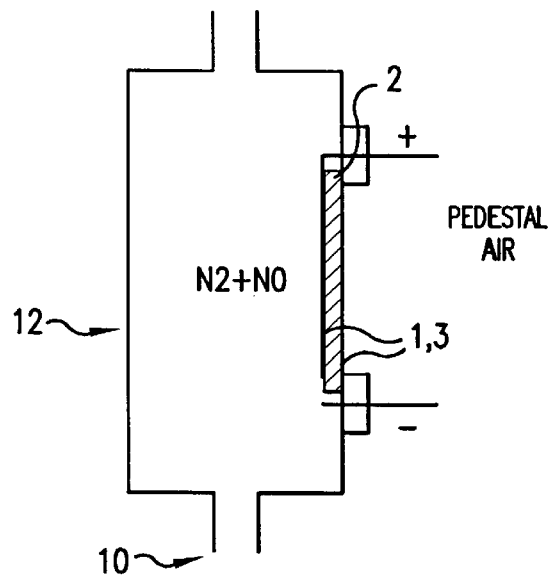
FIG. 4 is a view of the experimental setup for producing an NO-conducting solid electrolyte according to the invention by means of a gas phase exchange.

Test gas (exhaust gas) 10 and air 12 are separated by a gas-tight layer (molded body) of an $NO^+$-conducting solid electrolyte (FIG. 4). The solid electrolyte may have a layer thickness of <500 μm; a maximum crystallite size of 40 μm; and an ion conductivity resistance of <5 ohms/cm. On the porous electrolytes (preferably platinum) situated on both sides, the redox-reaction NO<--->$NO^+$ takes place and forces a potential between the electrodes that is determined by the concentration gradient. The potential is a direct function of the logarithmic concentration difference of the two sides; that is, when air is used as the reference, it is proportional to the logarithm of the NO-concentration in the exhaust gas. In contrast to the NO-sensor according to U.S. Pat. No. 5,466,350, which must be operated amperometrically, the operating principle described here is purely potentiometric and corresponds to that of the λ-probe with its known advantages.

Figure 1:
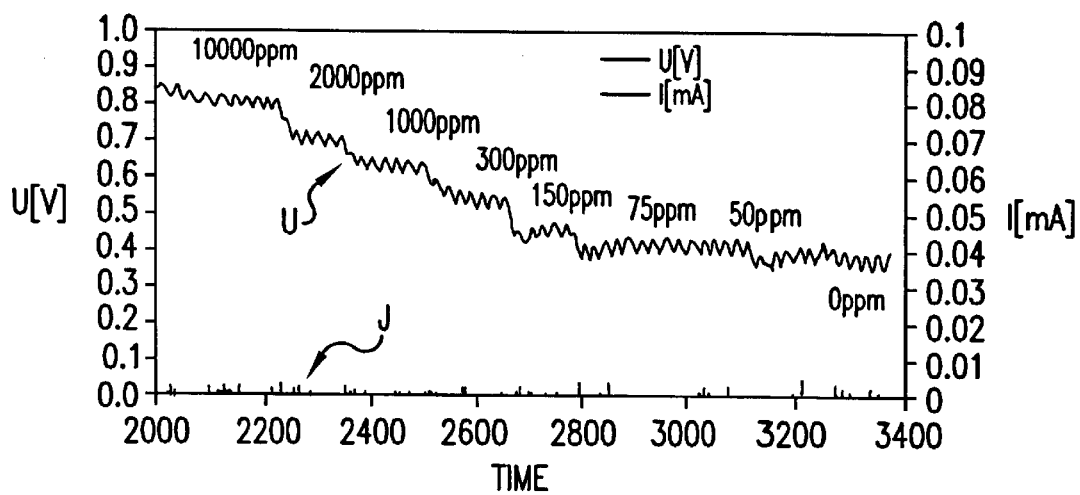
FIG. 1 is a graph of the voltage of the NO-sensor according to the invention (NO-β"-$Al_2O_3$) under currentness conditions for different NO-concentrations (1%, 0.2%, . . . 60 ppm) over time.

Using NO-β"-$Al_2O_3$, FIG. 1 shows that even 60 ppm NO in the exhaust gas produces an easily measurable voltage.

Figure 2:
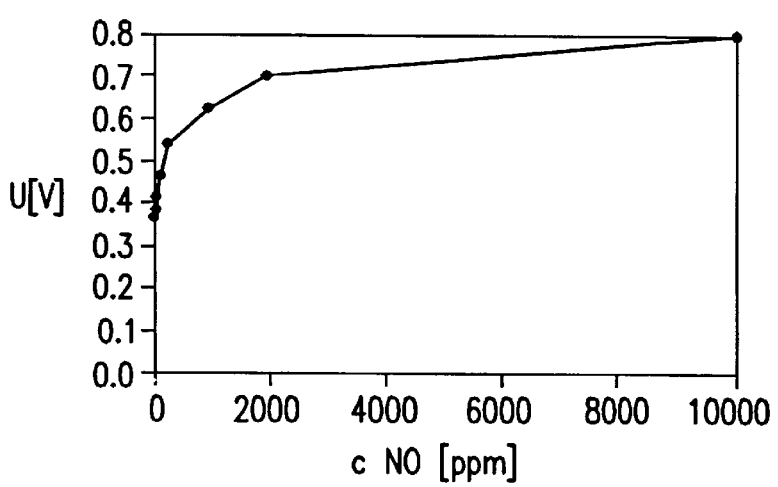
FIG. 2 is a graph of the dependence of the voltage of the NO-sensor according to the invention on the NO-concentration.

Furthermore, FIG. 2 shows that the highest voltage changes with the concentration occur in the concentration range of 0-2,000 ppm NO which is relevant to the use as an exhaust gas sensor.

If the gases differ on both sides of the electrolyte with respect to their NO-concentration, according to Nernst's Law, a potential difference occurs between the two electrodes:

$$U = R \times T/F \times ln$$

(pNO, measuring gas/pNO, reference),
 wherein
 R=the ideal gas constant,
 T=the temperature, in K, and
 F=Faraday's constant.

This potential difference represents the two standard potentials which occur on the anode as a result of the concentration difference between NO in the measuring gas and $NO^+$ in the solid electrolyte and on the cathode between the concentration of NO in the reference and $NO^+$ in the solid electrolyte. In contrast to the amperometrically operated sensor, the NO on the anode does not have to be oxidized to $NO^+$ and on the cathode it does not have to be reduced to NO for a potential difference to be recorded.

By selecting the NO partial pressure on the reference gas side, the measuring range as well as the sensitivity of the sensor can be adapted to the required NO concentration range. If the NO partial pressure in the reference gas is in the same order than in the measuring gas, the signal curve will be very steep; in the case of a higher partial pressure, differences between both sides will result in a flatter curve.

Since the output voltages also depend on the temperature, an electronic compensation must be carried out by way of a thermoelement thermistor if the temperature fluctuates.

A diffusion barrier is not required because no conversion of NO takes place on the electrodes and thus the diffusion to the electrode plays no role. The sensor is therefore also insensitive to fluctuating gas flow rates.

Production of the $NO^+$-Conducting Solid Electrolyte

Figure 3:
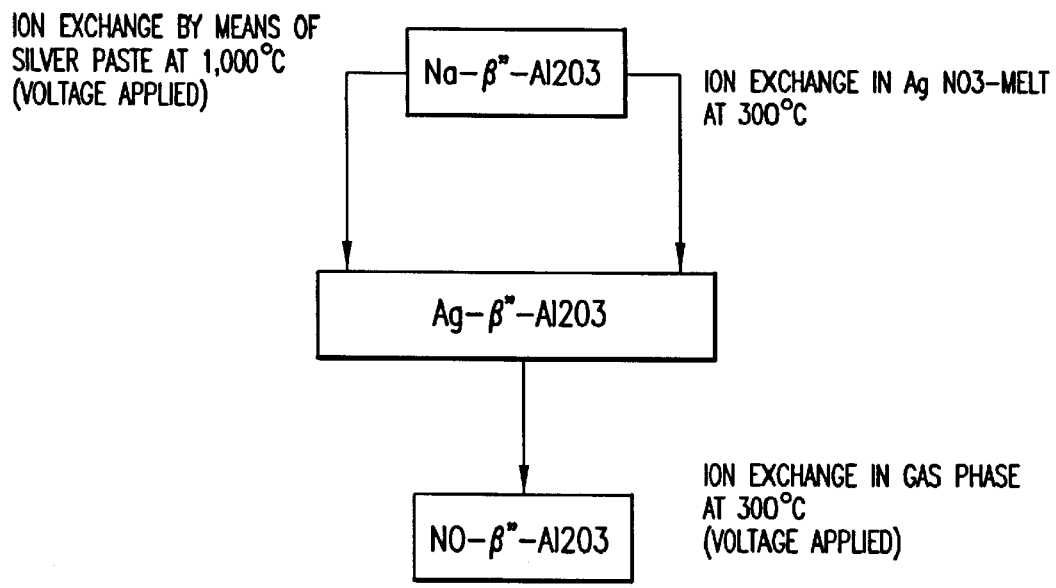
FIG. 3 is a chart of several process variants for producing an NO-β"-$Al_2O_3$ solid electrolyte according to the invention.

FIG. 3 shows various advantageous process variants for producing an $NO$-$\beta''$-$Al_2O_3$ solid electrolyte with $Na$-$\beta''$-$L_2O_3$ as the starting material used as an example.

1st Step: Ion exchange $Ag^+$ for $Na^+$ in an $AgNO_3$-melt at approximately 300° C. or by means of an anode coating with silver paste with an applied voltage and at approximately 1,000° C.

2nd Step: Ion exchange $NO^+$ for $Ag^+$ in the gas phase with an applied voltage and at approximately 300° C.

The use of Li-stabilized $\beta''$-$Al_2O_3$ with an $NaAlO_2$-content of <0.5% by weight is particularly advantageous. As a result, the conductivity and the water stability are considerably improved in comparison to $Na$-$\beta$-$Al_2O_3$ (J. L. Sudworth, A. R. Tilley, "The Sodium Sulfur Battery", Chapman and Hall 1985, Pages 20–56).

Therefore, a degree of exchange of >99% is also achieved during the ion exchange of $Na^+$ for $Ag^+$ in the $AgNO_3$-melt. This decisively improves the hydrolysis sensitivity of the sensor because only traces of sodium or $NaAlO_2$ will still be contained in the exchanged electrolyte.

For exchanging the $Ag^+$ for $Na^+$ ions in the melt, after the construction of the sensor, the solid electrolyte may also be coated on the anode with a silver paste. When a melt temperature of Ag (961° C.) is reached, and a sufficiently high voltage is applied between the anode and the cathode, a current conduction is measured which is the result of the ion exchange $Ag^+$ for $Na^+$. This exchange should take place under inert gas.

Before the ion exchange, the electrolyte may be cleaned of possible—ion-exchange-inhibiting—cover layers (NaOH and $Na_2CO_3$) in that, before the application of the voltage, the electrolyte is heated to above 850° C.

For the ion exchange of $Ag^+$ for $NO^+$ in the gas phase, the sensor construct is heated to 300° C. and is acted upon on the anode side by NO-containing carrier gas. When a sufficiently high voltage is applied between the anode and the cathode, a current conduction is measured due to the ion exchange of $NO^+$ for $Ag^+$. The electrolyte is not damaged by a cleaning in $H_2O$ because no salt melt has to be removed. The cathodically precipitated metallic silver remain as an electrode on the electrolyte surface.

The first step ($Ag^+$ vs $Na^+$) is not a prerequisite for the ion exchange. A direct-exchange $NO^+$ vs $Na^+$ is also possible with the above mentioned method.

However in this case, two disadvantages can be observed:

The degree of exchange cannot be determined easily by density measurements (because $Na^-$ and NO have similar atomic weights) and the exchanged $Na^+$ has to be removed after the ion exchange.

The ion exchange process can also be performed using other ion conductive solid state materials such as:

Me-$\beta$-$Al_2O_3$, wherein Me=$Li^+$, $Na^+$, $K^+$, $Rb^+$, $NH_4^+$, $Ag^+$;

Me-$\beta''$-$Al_2O_3$, wherein Me=$Li^+$, $Na^+$, $K^+$, $Rb^+$, $NH_4^+$, $Ag^+$;

Li-stabilized $\beta''$-$Al_2O_3$, having a lithium oxide content between 0.6 to 1.0% by weight and a sodium oxide content between 8.0 and 10.0% by weight;

$\beta$-ferrites ($Fe_2O_3$)

$\alpha$-corundum;

sodalites;

natural and synthetic laminated silicates oxidic frame structures in a pyrochlor or defect pyrochlor structure of the general formula $ABO_3$, where A=monovalent cations and B is at least one of Sb, Nb, W, Ta;

zeolites, zeolite-related frame structures;

hydrated $V_2O_5$;

vanadates and phosphates;

scheelites; and argyrodites of the formula $Ag_xMX_6$ wherein x=7–9, M=metal and X is selected from the group consisting of S, Se, Te

Embodiment: Gas Phase Exchange of the Solid Electrolyte

A complete Ag-$\beta''$-$Al_2O_3$ solid electrolyte 2 is contacted on both sides by electrodes 1, 3 and is included into a gas-tight chamber such that it is exposed to NO-containing carrier gas only on one side, as illustrated by FIG. 4. The membrane is heated to at least 300° C. for example by way of the gas flow being heated, to achieve a sufficient ion conductivity of the electrolyte. The NO-facing electrode acts as an anode, whereas the cathode is surrounded by air.

Figure 5:
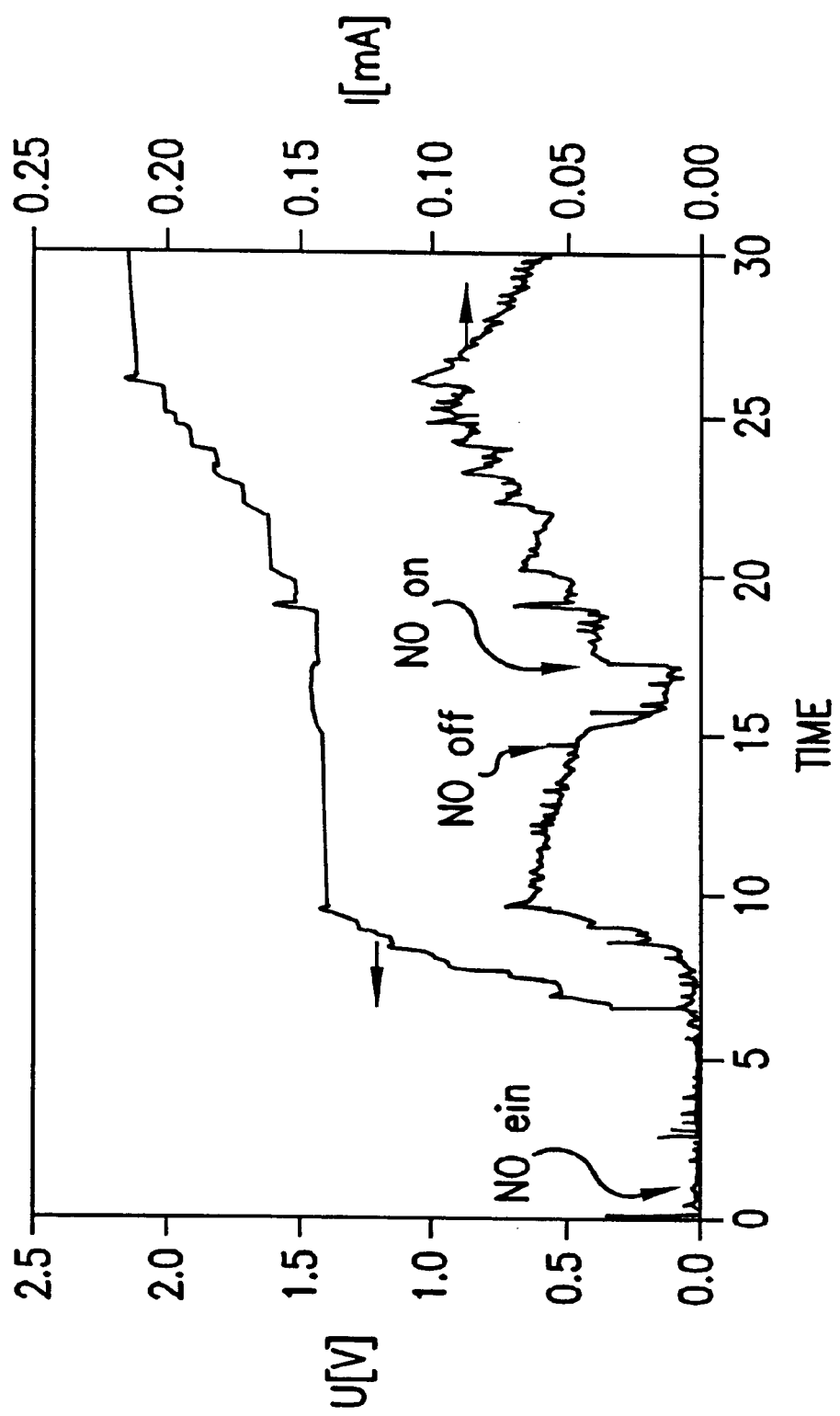
FIG. 5 is a graph of the time sequence of the voltage and the current intensity when $NO^+$ is included in the solid electrolytes during the gas phase exchange.

FIG. 5 represents the time sequence of the current and the voltage during ion exchange. A voltage is applied which is slowly increased. When the redox potential of $NO/NO^+$ is reached, a current will flow which increases with the voltage. Because of polarization, the current decreases slightly while the voltage is constant.

At a constant voltage, current conduction will decrease rapidly after NO is switched off and will be present again after NO is switched on again. As a result, the observed current is clearly the result of the following events:

1. Oxidation of NO to $NO^+$ on the anode;
2. Transport of $NO^+$ through the electrolyte (ion exchange);
3. Reduction of $NO^+$ to NO on the cathode.

Since at the beginning the electrolyte was charged completely with $Ag^+$, an ion exchange must have taken place of $NO^+$ for $Ag^+$. For calculating the required amount of substance for an arbitrary exchange of $Me^+$ (Me denotes a singly positive charged metal ion) for $NO^+$, the electrolysis duration can be determined directly; that is, electrolysis duration directly determines the degree of exchange by means of summarizing the ionic current. Since, during electrolysis, elemental metal or corresponding oxides/hydroxides precipitate on the working electrode, inclusion of $NO^+$, in addition to current/time measuring, can also be followed gravimetrically; therefore a further analysis is needless.

Gases and Solid Electrolytes to be used Advantageously for the Gas Phase Exchange Pure NO as well as oxygen-free NO-containing carrier gases or gas mixtures are suitable for use as the gas phase.

Anhydrous, cation-conducting solid states are suitable as preliminary stages for $NO^+$-exchanged solid electrolytes. These include:

Me-$\beta$-$Al_2O_3$, where Me may be $Li^+$, $Na^+$, $K^+$, $Rb^+$, $NH_4^+$, $Ag^+$ Me-$\beta''$-$Al_2O_3$, where Me may be $Li^+$, $Na^+$, $K^+$, $Rb^+$, $NH_4^+$, $Ag^+$ $\beta$-ferrites ($Fe_2O_3$)

$\alpha$-corundum sodalites natural and synthetic laminated silicates oxidic frame structures in a pyrochlor or defect pyrochlor structure of the general formula $ABO_3$, where A monovalent cations and B=Sb, Nb, W, Ta, as well as combinations of these elements, such as B=NbTa zeolites, zeolite-related frame structures, such as AlPOs or SAPOs, as well as mesoporous metal oxides;

hydrated $V_2O_5$ vanadates and phosphates scheelites, such as $Ca_{1-x}Ag_xWO_4$ argyrodites $Ag_xMX_6$(x=7–9, M=metal; X=S, Se, Te), such as $Ag_7TaS_6$, $Ag_8GaSe_6$.

The foregoing disclosure has been set forth merely to illustrate the invention and is not intended to be limiting. Since modifications of the disclosed embodiments incorporating the spirit and substance of the invention may occur to persons skilled in the art, the invention should be construed to include everything within the scope of the appended claims and equivalents thereof.

What is claimed is:

1. An apparatus for selective detection of NO in a gas, comprising:
   two porous electrodes;
   a nitrosonium conducting solid electrolyte positioned between the two electrodes; and
   means for measuring a voltage difference between the two porous electrodes, wherein the solid electrolyte is produced by a process comprising:
   performing, as a preliminary stage, an exchange reaction on a cation-conducting solid state material with Ag+being exchanged for a cation; and
   performing, in a gas phase, an exchange reaction wherein $NO^+$ is exchanged for $Ag^+$.

2. The apparatus according to claim 1, wherein the preliminary stage includes at least one member selected from the group consisting of:
   Me-$\beta$-$Al_2O_3$, wherein Me=$Li^+$, $Na^+$, $K^+$, $Rb^+$, $NH_4^+$, $Ag^+$;
   Me-$\beta''$-$Al_2O_3$, wherein Me=$Li^+$, $Na^+$, $K^+$, $Rb^+$, $NH_4^+$, $Ag^+$;
   Li-stabilized $\beta''$-$Al_2O_3$, having a lithium oxide content between 0.6 to 1.0% by weight and a sodium oxide content between 8.0 and 10.0% by weight;
   $\beta$-ferrites ($Fe_2O_3$);
   $\alpha$-corundum;
   sodalites;
   natural and synthetic laminated silicate;
   oxidic frame structures in a pyrochlor or defect pyrochlor structure of a general formula $ABO_3$, wherein A=monovalent cations and B is at least one of Sb, Nb, W, Ta;
   zeolites and zeolite-related frame structures;
   hydrated $V_2O_5$;
   vanadates and phosphates;
   scheelites; and
   argyrodites of the formula $Ag_xMX_6$ wherein x=7–9, M=metal and X is selected from the group consisting of S, Se and Te.

3. The apparatus according to claim 2, wherein the cation-conducting solid state material is a zeolite related frame structures selected from the group consisting of AlPOs, SAPOs, mesoporous metal oxides, and mixtures thereof.

4. The apparatus according to claim 2, wherein the cation-conducting solid state material is a scheelites comprising a compound having the formula $Ca_{1-x}Ag_xWO_4$.

5. The apparatus according to claim 2, wherein the cation-conducting solid state material is an argyrodite selected from the group consisting of $Ag_7TaS_6$ and $Ag_8$-$GaSe_6$.

6. An apparatus according to claim 1, wherein the solid electrolyte is Li-stabilized NO-$\beta''$-$Al_2O_3$.

7. An apparatus according to claim 1, wherein the solid electrolyte is Li-stabilized.

8. An apparatus according to claim 1, wherein said cation-conducting solid state material is Na-$\beta''$-$Al_2O_3$.

9. An apparatus for selective detection of NO in a gas, comprising:
   two porous electrodes;
   a nitrosonium conducting solid electrolyte positioned between the two electrodes; and
   means for measuring a voltage difference between the two porous electrodes,
   wherein the solid electrolyte is produced by a process comprising:
   performing, in a gas phase, an exchange reaction on a cation-conducting solid state material with $NO^+$ being directly exchanged for a cation.

* * * * *